US006367314B1

(12) United States Patent
Melton, Jr.

(10) Patent No.: US 6,367,314 B1
(45) Date of Patent: Apr. 9, 2002

(54) FUNCTIONAL STATUS ASSESSMENT SCALE

(75) Inventor: Hewlett E. Melton, Jr., Sunnyvale, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/489,446

(22) Filed: Jan. 21, 2000

(51) Int. Cl.$^7$ .................................................. G01N 1/00
(52) U.S. Cl. ................... 73/65.09; 73/862.046
(58) Field of Search .................... 73/862.041, 862.042, 73/862.043, 862.044, 862.045, 862.046, 65.01, 65.07, 65.09

(56) References Cited

U.S. PATENT DOCUMENTS

| | | | |
|---|---|---|---|
| 4,598,717 A | | 7/1986 | Pedotti ........................ 128/779 |
| 5,276,432 A | * | 1/1994 | Travis ......................... 73/65.01 |
| 5,388,591 A | | 2/1995 | De Luca et al. ............. 128/779 |
| 5,515,419 A | * | 5/1996 | Sheffer .......................... 379/58 |
| 5,609,162 A | * | 3/1997 | Blumentritt et al. ......... 128/782 |
| 5,627,327 A | | 5/1997 | Zanakis ................... 73/862.042 |
| 5,678,448 A | * | 10/1997 | Fullen et al. .................. 73/779 |
| 5,930,152 A | * | 7/1999 | Dumont et al. ......... 364/528.37 |

* cited by examiner

Primary Examiner—Max Noori (57) ABSTRACT

A system and a method of objectively assessing the functional status of a subject utilize a functional status scale to extract objective measures that are indicative of the subject's functional status. The objective measures are extracted from center-of-weight (C.O.W.) data gathered from the functional status scale when the subject is standing on the scale. These objective measures can then be used to assess the current functional status of the subject by a health care provider. The functional status scale can be remotely stationed at the subject's home, which eliminates the need for office visits, expensive home nurse visits, telephone interviews or video visits to assess the current functional status of the subject. The functional status scale includes weight sensors that are connected to a C.O.W. computer. The C.O.W. computer is configured to compute x and y coordinates of the C.O.W. from weight signals generated by the weight sensors. These x and y coordinates are then used to extract the objective measures by analysis modules. The objective measures may be statistical measures, frequency domain measures, or other analytical measures that can be utilized for assessment of a subject's functional status. In one configuration, the analysis modules are included in remote computers that can access a heath care provider's patient database, which receives and stores the x and y coordinates from the functional status scale. In an alternative configuration, the analysis modules are included in the functional status scale.

15 Claims, 12 Drawing Sheets

FUNCTIONAL STATUS ASSESSMENT SCALE

TECHNICAL FIELD

The invention relates generally to medical assessment devices and more particularly to a system and a method for assessing the functional status of a subject.

DESCRIPTION OF THE RELATED ART

Functional status forms an important component in the assessment of a patient's clinical course. The abilities to stand, walk a prescribed distance, or perform routine daily tasks are examples of activities that provide general classification levels for functional status. Gathering information related to functional status of a patient generally requires the judgment of a clinical observer or requires the use of a validated self-assessment questionnaire. Patient difficulties in maintaining balance are intimately tied to their functional status. For patients who are very unsteady, the act of standing is sometimes a major accomplishment. The patient may wobble significantly and visibly as he/she goes through the process of standing. Patients having better balance control wobble less and enjoy higher levels of activity, and consequently, they have a higher functional status. Thus, a patient's wobbling is a cue for a low level of functional status.

There are number of prior art systems that are useful in testing the ability of a patient to control his/her balance. U.S. Pat. No. 5,627,327 to De Luca et al. describes a system and a method for analyzing the postural control ability of a patient. The system of De Luca et al. includes a force platform, which is connected to a processor. The force platform is used to derive the center of pressure when a patient stands on the platform. The system generates a stabilogram diffusion plot by computing the mean square displacement of the center of pressure over time. The system can then calculate a Brownian diffusion coefficient, which is indicative of the level of stochastic activity of the center of pressure, from the slope of the stabilogram diffusion plot.

U.S. Pat. No. 5,627,327 to Zanakis describes a system for determining the physical instability of a patient. The system of Zanakis includes a stable platform that generates signals, which depend on the magnitude and direction of the force applied to the face of the platform. The system also includes a convex rocker dish with a flat surface on which a patient stands. The curved side of the rocker dish is placed on the platform. Thus, the convex rocker dish is an unsteady structure. The platform is connected to a display screen via a computer. The signals from the platform are used to generate a cursor on the screen. The position of the cursor is made to vary, depending the orientation of the flat surface on the rocker dish with respect to the face of the platform. Therefore, a patient standing on the rocker dish is able to manipulate the cursor on the screen by changing the orientation of the rocker dish. The physical instability of the patient is determined by measuring the time required for the patient to move the cursor to a target area on the screen by manipulating the rocker dish.

Although these known systems operate well for their intended purpose, what is needed are a system and a method for objectively assessing the functional status of a patient.

SUMMARY OF THE INVENTION

A system and a method of objectively assessing the functional status of a subject utilize a functional status scale to extract objective measures that are indicative of the subject's functional status. The objective measures are extracted from center-of-weight (C.O.W.) data gathered from the functional status scale when the subject is standing on the scale. These objective measures can then be used to assess the current functional status of the subject by a health care provider. The functional status scale can be remotely stationed at the subject's home, which eliminates the need for office visits, expensive home nurse visits, telephone interviews or video visits to assess the current functional status of the subject.

The system includes a communications hub that allows the functional status scale to be connected to a traditional wired telephone communications provider or to a cellular phone communications provider via a wireless connection when a direct wire connection is not possible. The system also includes a health care provider's patient database, which is connected to the traditional telephone communications provider and the cellular phone communications provider. Thus, information from the functional status scale can be transmitted to the patient database through either a wireless connection via the communications hub or a direct wire connection via the traditional telephone communications provider. The patient database may be embodied in a computer, which allows a health care provider to directly access the stored information in the database. The patient database can be linked to the Internet or other network, such as a LAN or WAN, so that the stored information in the database can be accessed by remote computer through one of these established communications infrastructures.

The functional status scale includes weight sensors that are connected to a C.O.W. computer. Each of these weight sensors is designed to generate a weight signal that is proportional to the amount of vertical (downward) force on the weight sensor, when a subject stands on the scale. The C.O.W. computer is configured to generate signals that represent x and y coordinates of C.O.W. by processing the weight signals from the weight sensors. The C.O.W. computer is also configured to generate a signal that represents the weight of the subject.

The functional status scale also includes a processor, a storage device, a display and a communications interface module. The processor is connected to the C.O.W. computer to receive the signals computed by the C.O.W. computer. The signals that represent the C.O.W. can then be stored in the storage device or relayed to the communications interface module for transmission to the health care provider's patient database. The communications interface module includes a modem and a radio frequency (RF) transceiver. The modem is used to establish a wire connection with the traditional telephone communications provider, while the RF transceiver is used to establish a wireless connection with the communications hub. The signal that represents the weight of the subject can be processed by the processor to drive the display of the functional status scale to alphanumerically present the weight of the subject. Thus, the functional status scale can operate as a conventional weight scale.

The computers of the system that are used to access the health care provider's patient database include statistical and frequency domain analysis modules that are configured to extract the objective measures from the C.O.W. data transmitted from the functional status scale. These modules can be implemented as software and/or hardware. The statistical analysis module is configured to extract statistical measures that can be utilized for assessment of a subject's functional status. Examples of statistical measures that may be extracted by the statistical analysis module include maximum x and y coordinate values, autocovariance of x and y, autocovariance of time (response time), standard deviation of x and y, mean magnitude excursions for x and y, maximum rate of change for x and y, statistical run length with short and long emphasis, cross correlation coefficient between x and y, cross-covariance between x and y, and cross-covariance length. The frequency domain analysis module is configured to extract frequency domain measures that can be utilized for functional status assessment. Examples of frequency domain measures that may be extracted by the frequency domain analysis module include dominant frequency for x and y coordinates, phase for the dominant frequency, mean power bandwidth, amplitude rank (largest to smallest) of frequency components, phase rank (largest to smallest) of frequency components, means square phase, mean phase, mean frequency, rms frequency, and rms phase.

The computers of the system may include other analysis modules that utilize different analytical approaches, such as chaos and fractal analyses, to extract additional measures for assessment of a subject's functional status. In an alternative configuration, the analysis modules may be included in the functional status scale, rather than the remote computers. In this alterative configuration, the measures computed by the analysis modules are transmitted from the functional status scale to the health care provider's patient database, instead of the signals that represent x and y coordinates of the C.O.W.

In a first embodiment, the functional status scale includes four weight sensors that are positioned in a rectangular configuration. In a second embodiment, the functional status scale includes four weight sensors that are positioned in a diamond-like configuration. In a third embodiment, the functional status scale includes three weight sensors that are positioned in a triangular configuration. In each of these embodiments, the C.O.W. computer is configured accordingly to compute the x and y coordinate signals from the weight signals generated by the three or four weight sensors.

The method of objectively assessing the functional status of a subject in accordance with the invention includes a step during which weight signals are generated by weight sensors of a functional status scale in response to the subject's weight when the subject is standing on the scale. Using these weight signals, x and y coordinates of the center-of-weight are computed by a C.O.W. computer of the functional status scale. Next, a communications link is established between the functional status scale and a health care provider's patient database. The x and y coordinates are then transmitted to the health care provider's patient. Next, the x and y coordinates are analyzed by one or more analysis modules included in a remote computer that has communicated with the health care provider's patient database. During this step, functional status measures are extracted from the x and y coordinates by the analysis modules. The functional status measures may be derived by statistical analysis, frequency domain analysis or other analytical approaches. These functional status measures provide objective criteria for assessment of the current functional status of the subject.

DETAILED DESCRIPTION

Figure 1:
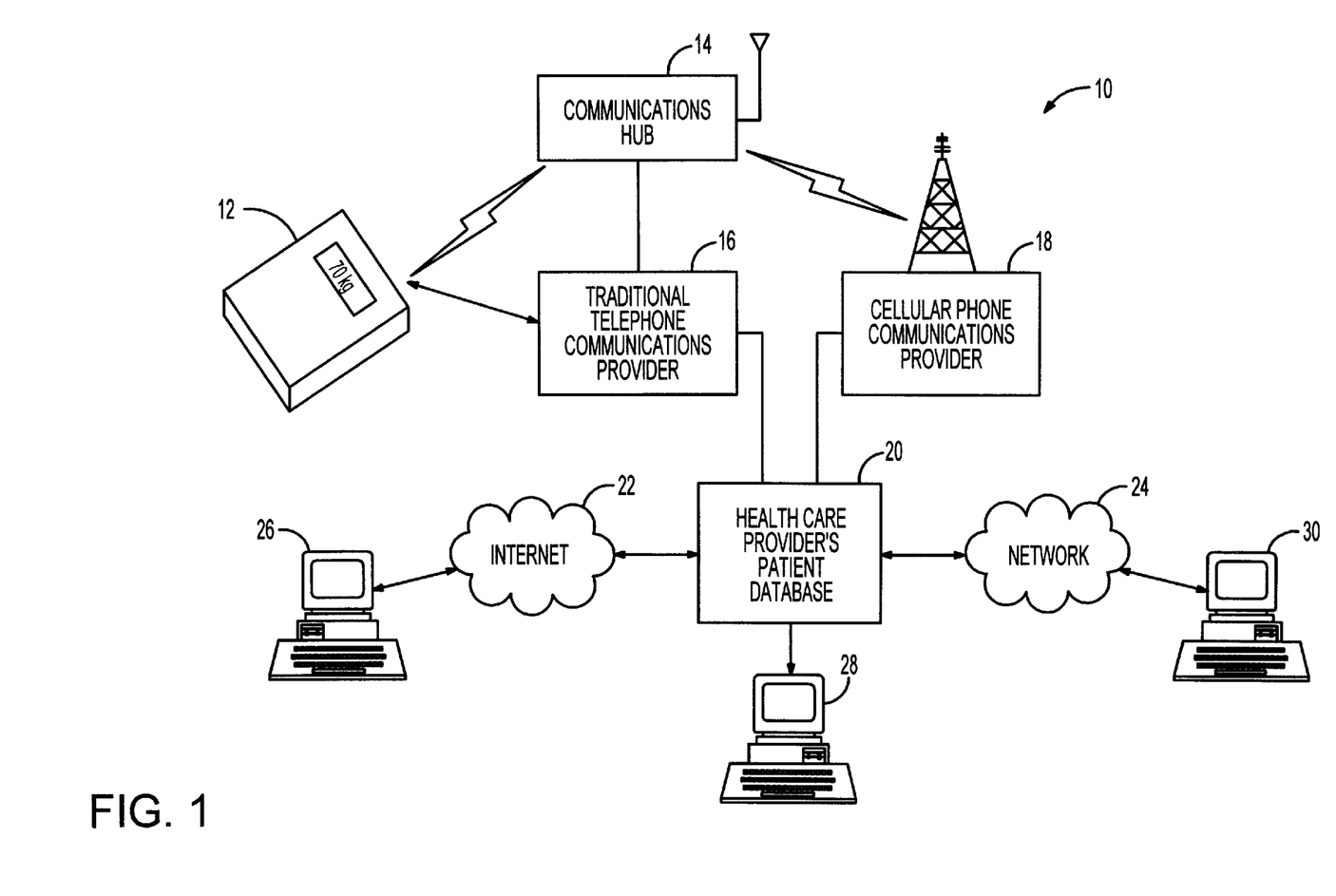
FIG. 1 is a schematic diagram of a system in accordance with the present invention.

With reference to FIG. 1, a system 10 for objectively assessing the functional status of a subject in accordance with the present invention is shown. The system includes a functional status scale 12 that operates to acquire information related to a subject's ability to maintain balance, as well as the weight information of the subject. The acquired information is then used to extract objective measures that are indicative of the current functional status of the subject. Thus, the functional status of the subject can be assessed objectively by examining these measures. The functional status scale can be remotely stationed at the subject's home, which eliminates the need for office visits, expensive home nurse visits, telephone interviews or video visits to assess the current functional status of the subject.

The system 10 further includes a communications hub 14 that can establish a communications link with either a traditional telephone communications provider 16 or a cellular phone communications provider 18. Preferably, the functional status scale 12 is designed such that it can be connected to the traditional telephone communications provider by a direct phone line connection or connected to the communications hub by a wireless connection. Thus, the communications hub provides a means for the functional status scale to establish a connection with the traditional telephone communications provider, or the cellular phone communications provider when a phone jack is not readily accessible.

The system 10 also includes a health care provider's patient database 20, which is connected to the traditional telephone communications provider 16 and the cellular phone communications provider 18. The patient database may be linked to the Internet 22 or another network 24, such as a LAN or WAN. The Internet, the patient database, and the network are connected to one or more computers 26, 28 and 30. For simplification, the Internet, the patient database, and the network are each shown to be connected to a single computer. After the information from the functional status scale 12 is transmitted to the health care provider's patient database, the received information can be accessed by a health care provider using one of the computers 26, 28 and 30. Using the computer 28, a health care provider may retrieve the functional status information of a particular patient by directly accessing the patient database. Although the health care provider's patient database is shown as a separate unit, the patient database may be included in the computer 28. The computer 30 provides a health care provider access to the patient database via the network. Alternatively, the functional status information may be e-mailed to the computers 26 and 30 via the Internet or the network, respectively. As another alternative, if the functional status information is uploaded to a website on the Internet, a health care provider may obtain the functional status information from the website by logging on to the Internet using the computer 26.

Figure 2:
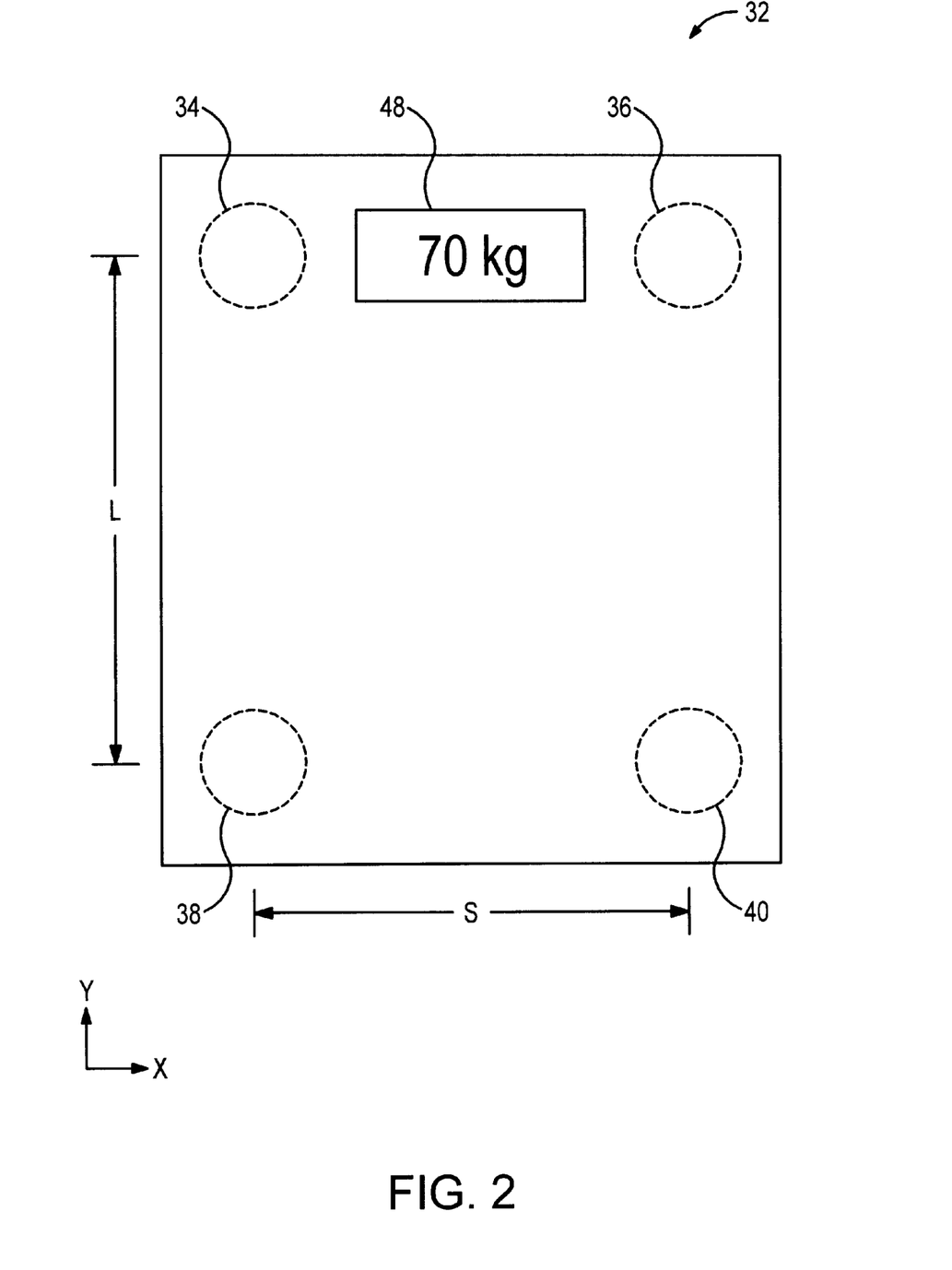
FIG. 2 is a top view of a functional status scale in accordance with a first embodiment of the invention.
Figure 3:
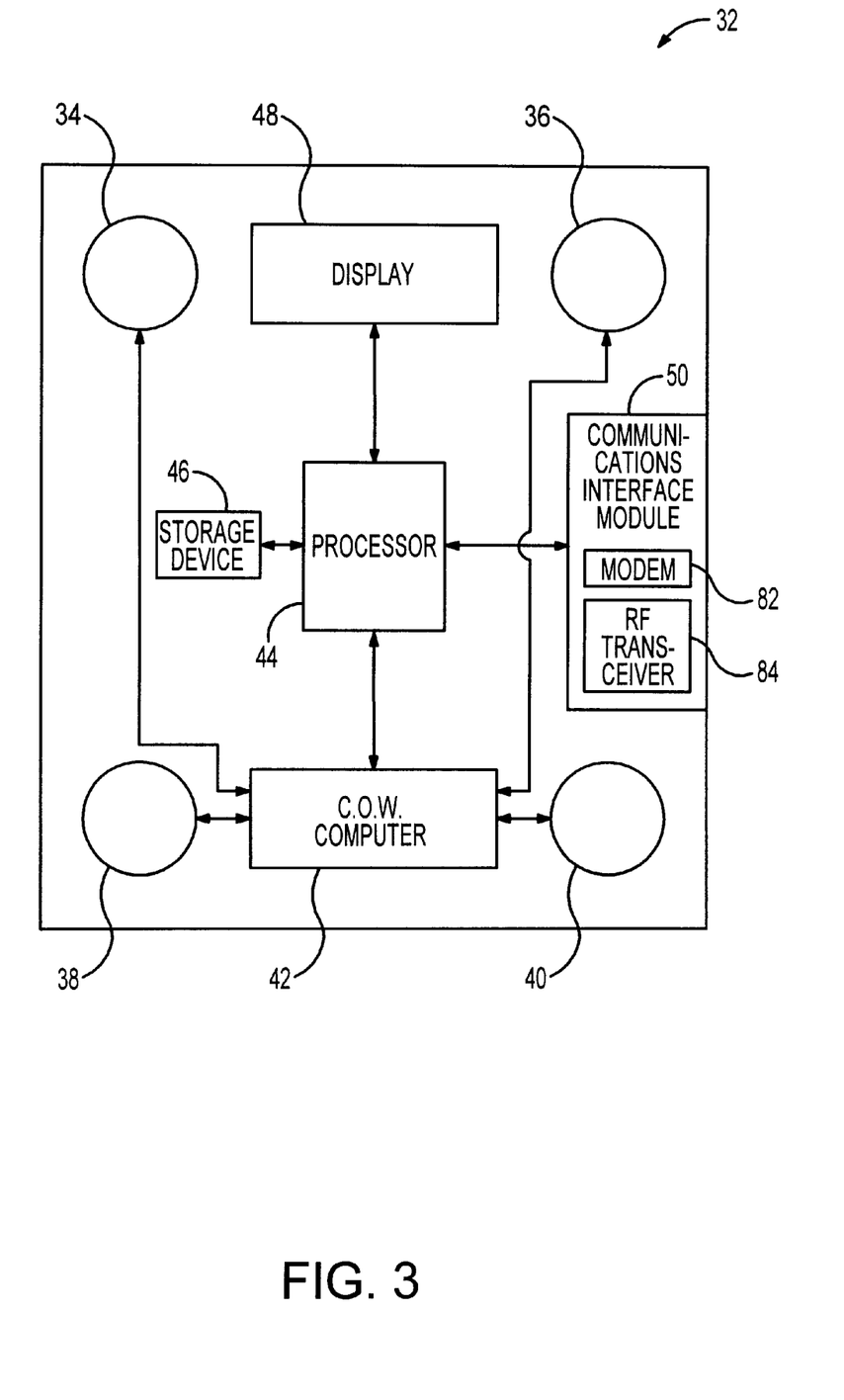
FIG. 3 is a block diagram of the components of the functional status scale of FIG. 2.

Turning now to FIGS. 2 and 3, a functional status scale 32 in accordance with a first embodiment of the invention is shown. FIG. 2 is a top view of the functional status scale. FIG. 3 is a block diagram, illustrating the components of the functional status scale. The functional status scale includes four weight sensors 34, 36, 38 and 40 that are positioned on the corners of the scale. Each of these sensors is configured to generate a weight signal in response to a force when a subject stands on the scale. The strength of a particular weight signal depends on the amount of force exerted on the sensor that produced that signal. As illustrated in FIG. 2, the weight sensors 34 and 38 are separated by a distance L, while the weight sensors 38 and 40 are separated by a distance S. Since the weight sensors 34, 36, 38 and 40 are positioned in a rectangular configuration, the weight sensors 36 and 40 are also separated by the distance L. Similarly, the weight sensors 34 and 36 are separated by the distance S.

The functional status scale 32 further includes a center of weight (C.O.W.) computer 42, a processor 44, a storage device 46, a display 48 and a communications interface module 50. The C.O.W. computer is configured to compute x and y coordinates of the C.O.W., using the weight signals from the weight sensors 34, 36, 38 and 40. Since the C.O.W. will vary as the subject shifts his/her weight, the coordinates generated by the C.O.W. generator will vary with time. The x and y coordinates of the C.O.W. can be computed by the following equation, which is derived by summing the torques on the functional status scale to zero.

$$-jW_x+iW_y=j(S/2)[-W2-W3+W1+W4]+i(L/2)[W1+W2-W3-W4], \quad (1)$$

where i and j are unit vectors for the x direction and the y direction, respectively, and where W1, W2, W3 and W4 are the weight signals generated by the weight sensors 34, 36, 38 and 40, respectively. Using equation (1), the x and y coordinates of the C.O.W. can be expressed as follows:

$$X=(S/2)[(W2+W3-W1-W4)/W] \quad (2)$$

and $$Y=(L/2)[(W1+W2-W3-W4)/W], \quad (3)$$

where W=W1+W2+W3+W4. Therefore, the C.O.W. computer 42 includes components to derive the x and y coordinates using the equations (2) and (3).

Figure 4:
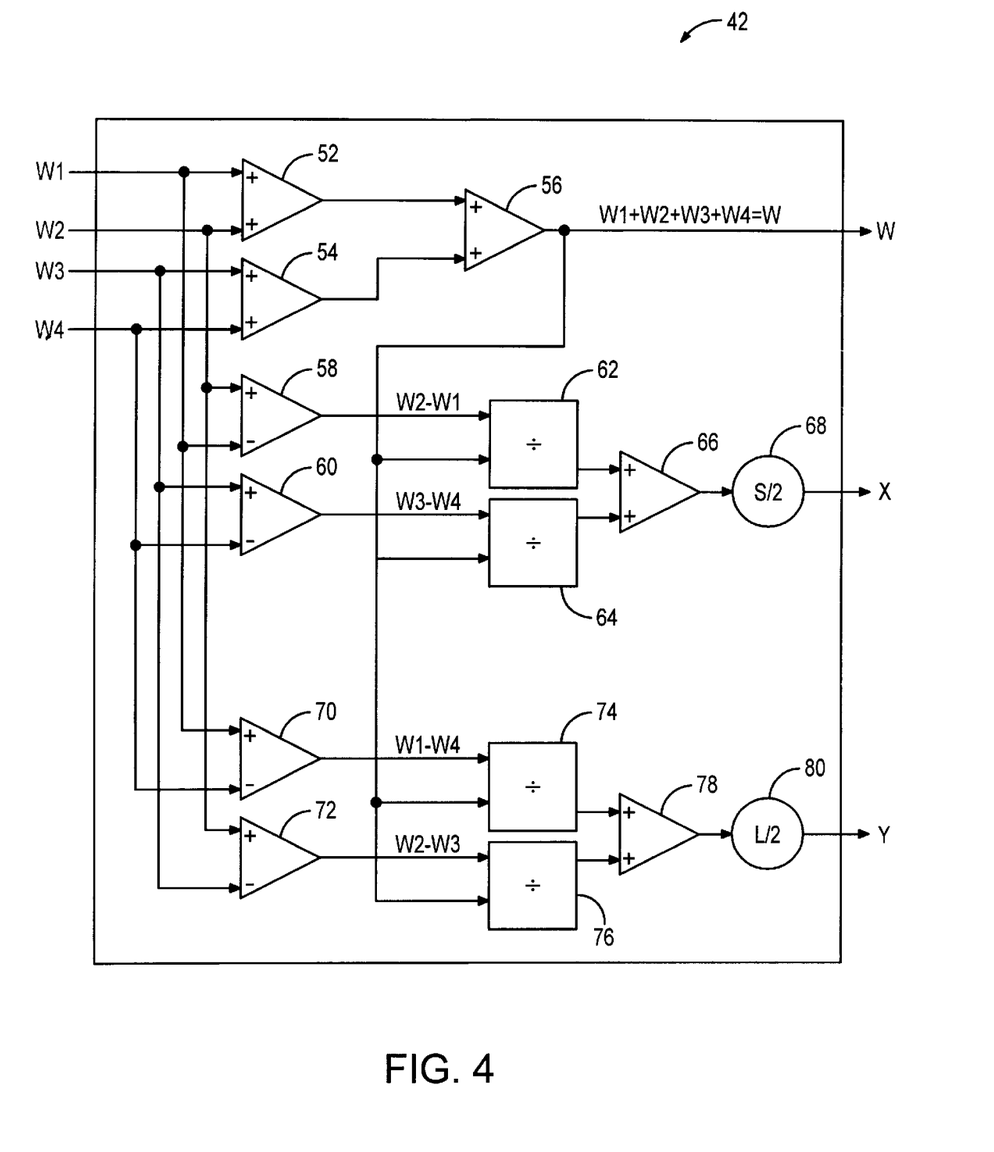
FIG. 4 is a block diagram of the components of a C.O.W. computer included in the functional status scale of FIG. 2.

In FIG. 4, the components of the C.O.W. computer 42 are shown in a block diagram form. The C.O.W. computer includes summing units 52, 54 and 56 that compute the current W by summing the weight signals W1, W2, W3 and W4 from the weight sensors 34, 36, 38 and 40. The C.O.W. computer also includes subtraction units 58 and 60, dividers 62 and 64, a summing unit 66, and a multiplier 68 that compute the x coordinate of the C.O.W. using the weight signals W1, W2, W3 and W4 and the computed W. The C.O.W. computer further includes subtraction units 70 and 72, dividers 74 and 76, a summing unit 78 and a multiplier 80 that compute the y coordinate of the C.O.W. These computed values, W, x coordinate and y coordinate, are transmitted to the processor 44 for signal processing.

Referring now back to FIG. 3, the processor 44 of the functional status scale 32 is coupled to the storage device 46, the display 48 and the communications interface module 50, as well as the C.O.W. computer 42. The processor is configured to control the display and the communications interface module. The display may be an LCD device that can alphanumerically display the measured weight W of the subject on the functional status scale. The communications interface module operates to provide a communications link between the functional status scale and the health care provider's database 20 to transmit the computed C.O.W. information, i.e., the x and y coordinates. The communications interface module includes a modem 82 that allows the functional status scale to be connected to the traditional telephone communications provider 16 via a telephone line. The communications interface module also includes a radio-frequency (RF) transceiver 84 that allows the functional status scale to be wirelessly connected to the communications hub 14. The wireless connection between the functional status scale 32 and the communications hub may facilitate a two-way communication between the functional status scale and a health care provider, who can also be connected to the communications hub via the traditional telephone communications provider 16 or the cellular phone communications provider 18.

Figure 5:
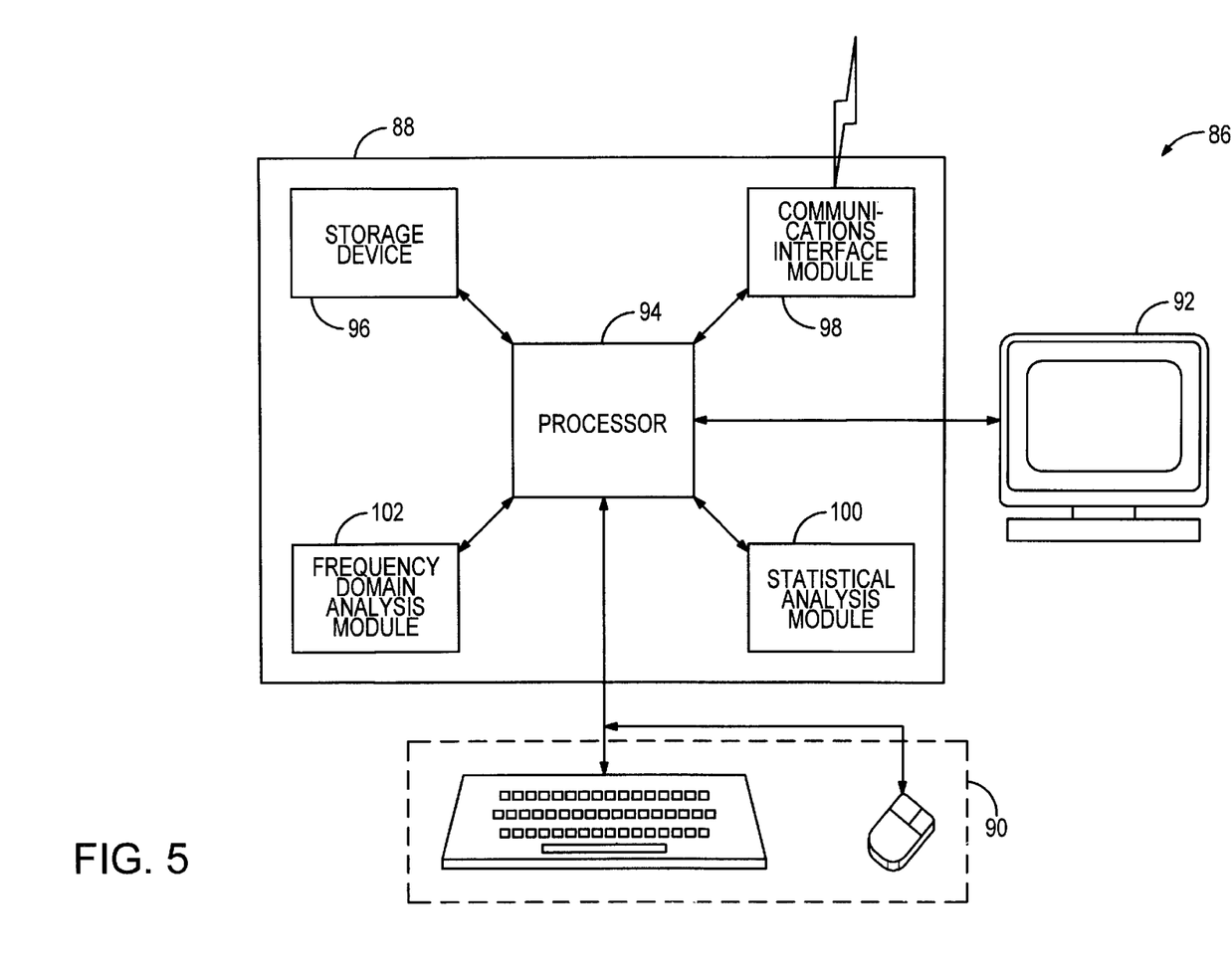
FIG. 5 is a block diagram of the components of an exemplary remote computer included in the system of FIG. 1.

In FIG. 1, the computers 26, 28 and 30 of the system 10 that are operatively connected to the health care provider's patient database 20 include one or more analytical modules to derive the objective measures that are indicative of a subject's functional status, using the C.O.W. information generated by the functional status scale 32. An exemplary computer 86 of the system is shown in FIG. 5. The computer includes a processing unit 88, an input device 90 and a monitor 92. The input device may include a standard keyboard and a computer mouse. The processing unit includes a processor 94, a storage device 96, a communications interface module 98, a statistical analysis module 100 and a frequency domain analysis module 102. The storage device and the processor may be known devices that are commonly found in personal computers. The communications interface module may include a modem or other device to allow the computer 86 to establish a communications link to the Internet 22 or the network 24. The statistical and frequency domain analysis modules 100 and 102 are configured to extract the objective measures from the x and y coordinates that are transmitted from the functional status scale 32. These modules can be implemented in the computer as software and/or hardware.

Figure 6:
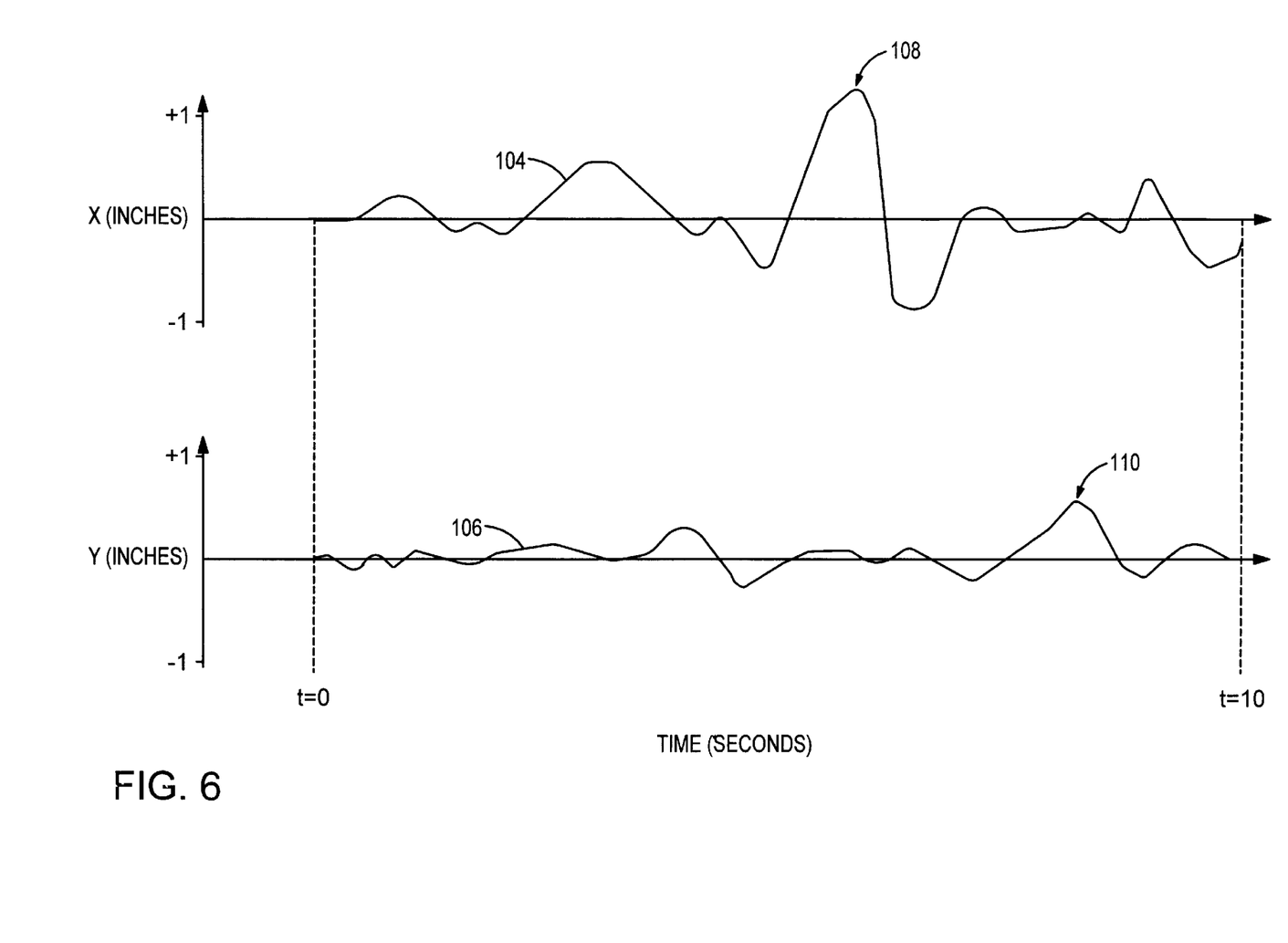
FIG. 6 shows sample x and y coordinates for center-of-weight.

In FIG. 6, sample x and y coordinates are plotted over a fixed duration of ten seconds. These x and y coordinates represent information that may be transmitted from the functional status scale 32 to the computer 86. Plotted line 104 represents the x coordinates, while plotted line 106 represents the y coordinates. The statistical analysis module 100 is configured to extract various statistical measures that can be utilized for assessment of a subject's functional status. As an example, the statistical analysis module 100 may be configured to extract the maximum x value 108 and the maximum y value 110 from the x and y coordinates. Examples of other statistical measures that may be computed by the statistical analysis module include: autocovariance of x and y, autocovariance time (response time), standard deviation of x and y, mean magnitude excursions for x and y, maximum rate of change for x and y, statistical run length with short and long emphasis, cross correlation coefficient between x and y, cross-covariance between x and y, and cross-covariance length.

Figure 7A:
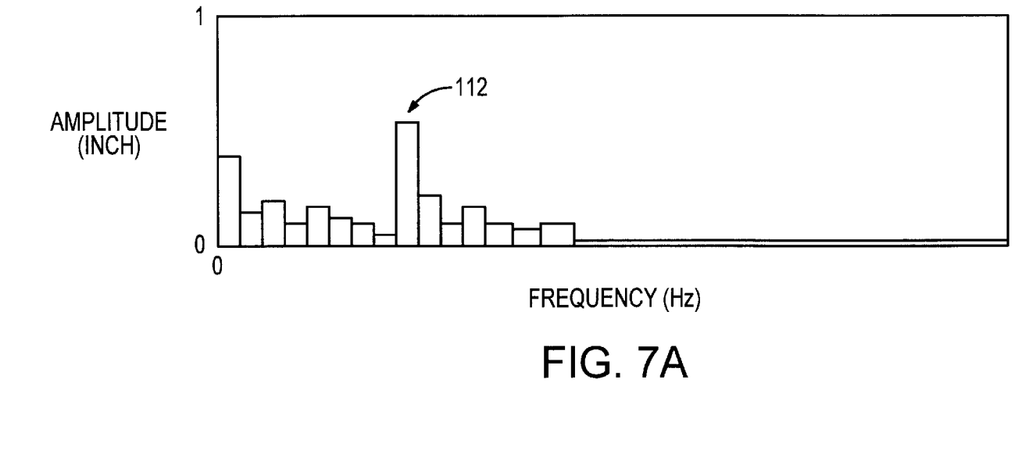
FIGS. 7A and 7B respectively show sample amplitude and phase information for sample x and y coordinates.
Figure 7B:
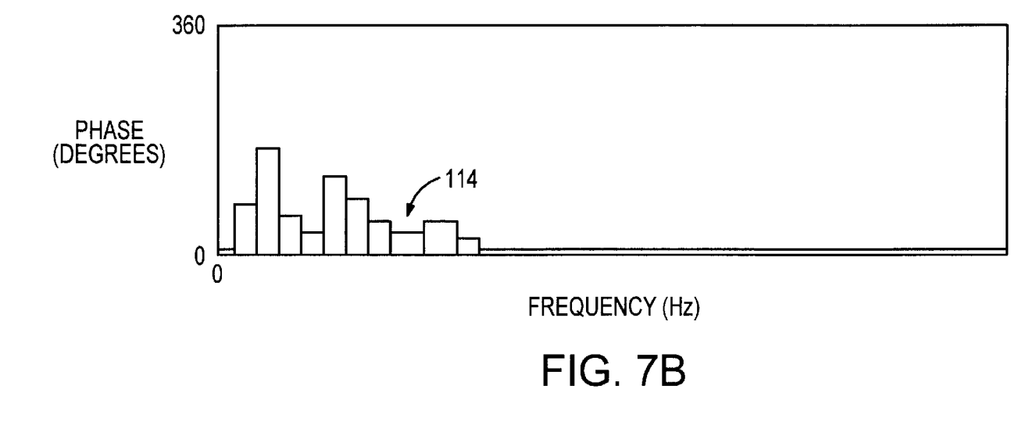

The frequency domain analysis module 102 operates to transform the x and y coordinates to a frequency domain as amplitude and phase versus frequency, as illustrated in FIGS. 7A and 7B, for sample values of x coordinates. Using Fourier analysis, the frequency domain analysis module is configured to extract frequency domain measures that can be utilized for assessment of a subject's functional status. As an example, the frequency domain analysis module may be configured to extract the dominant frequency 112 for the x coordinates and the phase 114 for the dominant frequency. Examples of other frequency domain measures for x and y that may be computed by the frequency domain analysis module include: mean power bandwidth, amplitude rank (largest to smallest) of frequency components, phase rank (largest to smallest) of frequency components, mean square phase, mean phase, mean frequency, rms frequency and rms phase.

The computer 86 may include other analysis modules that utilize different analytical approaches, such as chaos and fractal analyses, to extract additional measures for assessment of a subject's functional status. In an alternative configuration, the analysis modules 100 and 102 may be included in the functional status scale 32. In this alternative configuration, the measures computed by the analysis module are transmitted from the functional status scale to the health care provider's database 20, instead of the x and y coordinates.

Figure 8:
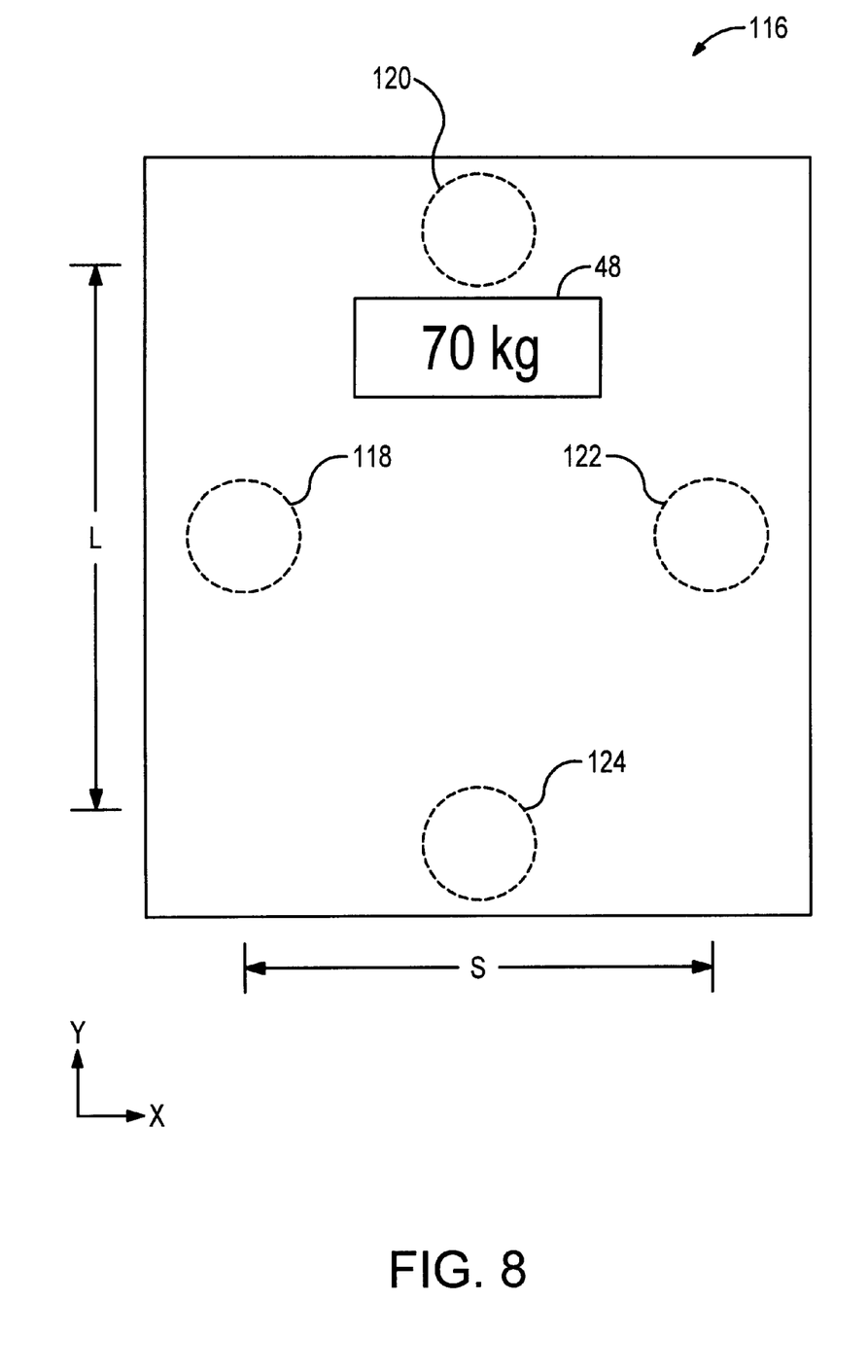
FIG. 8 is a top view of a functional status scale in accordance with a second embodiment of the invention.

Turning now to FIG. 8, a functional status scale 116 in accordance with a second embodiment of the invention is shown. In this embodiment, the functional status scale also includes four weight sensors 118, 120, 122 and 124. However, these sensors are positioned in a diamond-like configuration. The weight sensors 120 and 124 are separated by the distance L, while the weight sensors 118 and 122 are separated by the distance S. Although not completely shown, the functional status scale 116 also includes the display 48, the storage device 46, the processor 44 and the communications interface module 50 that are identical to those included in the functional status scale 32 of FIGS. 2 and 3. However, the functional status scale 116 includes a C.O.W. computer 126, shown in FIG. 9, that differs from the C.O.W. computer 42 of the functional status scale 32.

Since the weight sensors 118, 120, 122 and 124 are positioned in the diamond-like configuration, the relationship between the x and y coordinates of the C.O.W. and the weight signals from the sensors is different than in the first embodiment. In this diamond-like configuration, summing the torques to zero gives the following equation.

$$-jW_x+iW_y=j(S/2)[W1-W3]+i(L/2)[W2-W4], \quad (4)$$

where i and j are unit vectors for the x direction and the y direction, respectively, and where W1, W2, W3 and W4 are the weight signals generated by the weight sensors 118, 120, 122 and 124, respectively. Using equation (4), the x and y coordinates of the C.O.W. can be expressed as follows:

$$X=(S/2)[(W3-W1)/W] \quad (5)$$

and $$Y=(L/2)[(W2-W4)/W], \quad (6)$$

where $W=W1+W2+W3+W4$.

Figure 9:
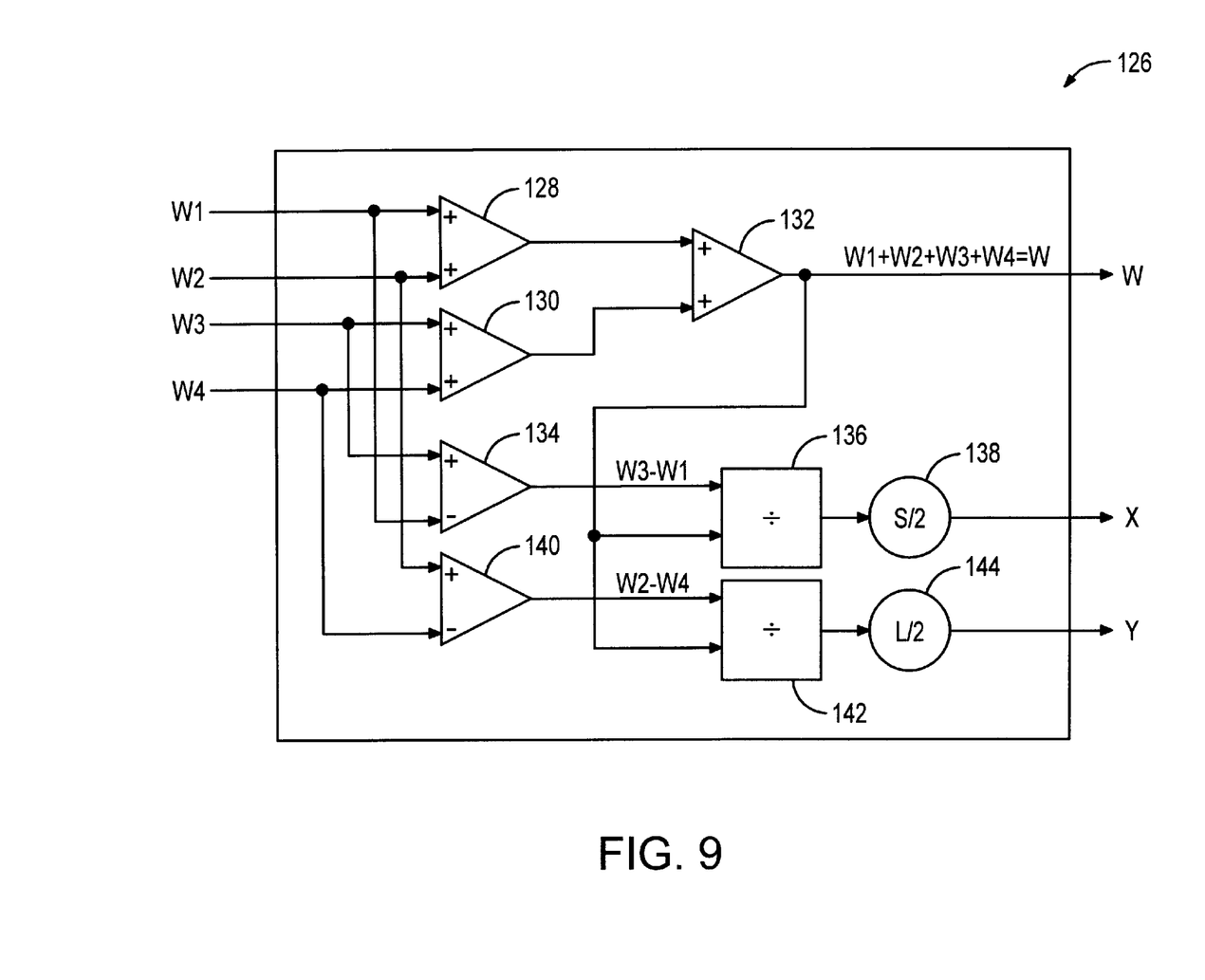
FIG. 9 is a block diagram of the components of a C.O.W. computer included in the functional status scale of FIG. 8.

The C.O.W. computer 126 is configured to use the equations (5) and (6) to derive x and y coordinates. In FIG. 9, the components of the C.O.W. computer are shown in a block diagram form. The C.O.W. computer includes summing units 128, 130 and 132 that compute the W by summing the weight signals W1, W2, W3 and W4 from the weight sensors 118, 120, 122 and 124. The C.O.W. computer also includes a subtraction unit 134, a divider 136 and a multiplier 138 that compute the x coordinate of the C.O.W., using the weight signals W1 and W3 and the computed W. The C.O.W. computer further includes a subtraction unit 140, a divider 142, and a multiplier 144 that compute the y coordinate of the C.O.W., using the wight signals W2 and W4 and the computed W. These computed values, W, x coordinate and y coordinate, are transmitted to the processor 44 of the functional scale 116 for signal processing.

Figure 10:
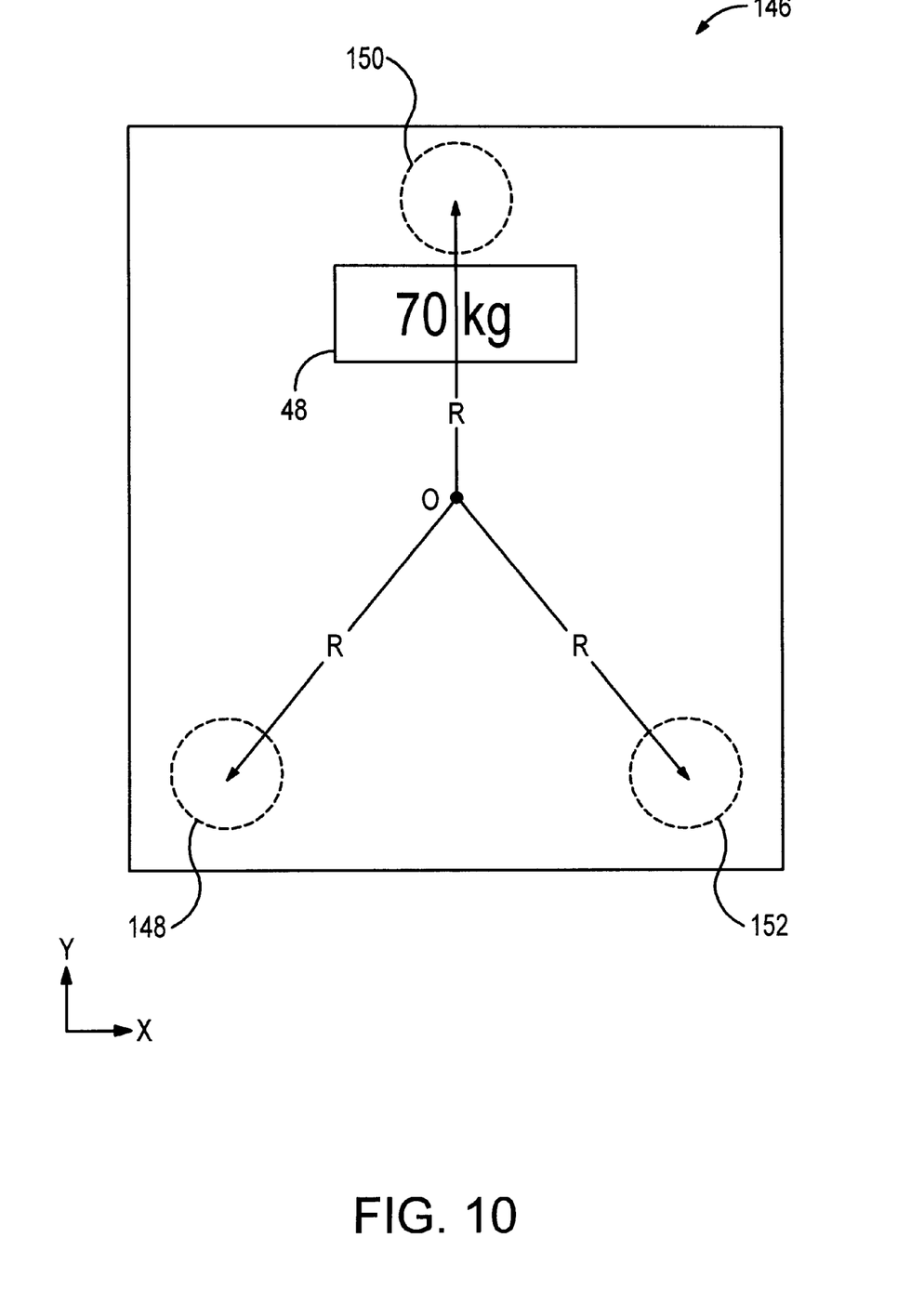
FIG. 10 is a top view of a functional status scale in accordance with a third embodiment of the invention.

Turning now to FIG. 10, a functional status scale 146 in accordance with a third embodiment of the invention is shown. In this embodiment, the functional status scale includes only three weight sensors 148, 150 and 152 that are positioned in a triangular configuration. Each weight sensor is located at a distance R from a reference point O, which forms an origin. Similar to the first and second embodiments, the functional status scale also includes the display 48, the storage device 46, the processor 44 and the communications interface module 50. The storage device, the processor and the communications interface module are not shown in FIG. 10. However, the functional status scale includes a C.O.W. computer 154, shown in FIG. 11, that differs from the C.O.W. computers 42 and 116 of the previous embodiments.

In this triangular configuration, the relationship between the x and y coordinates of the C.O.W. and the weight signals from the sensors 148, 150 and 152 can be derived in the following manner. Summing the torques on the functional scale 146 to zero gives the following equation.

$$jW_x+iW_y=j(3)^{1/2}R/2[W1-W3]+iR[W2-(W1)/2-(W3)/2], \quad (7)$$

where i and j are unit vectors for the x direction and the y direction, respectively, and where W1, W2 and W3 are the weight signals generated by the weight sensors 148, 150 and 152, respectively. Using equation (7), the x and y coordinates of the C.O.W. can be expressed as follows:

$$X=(3)^{1/2}(R/2)[(W3-W1)/W] \quad (8)$$

and $$Y=R[(W2-(W1)/2-(W3)/2)/W], \quad (9)$$

where $W=W1+W2+W3$.

Figure 11:
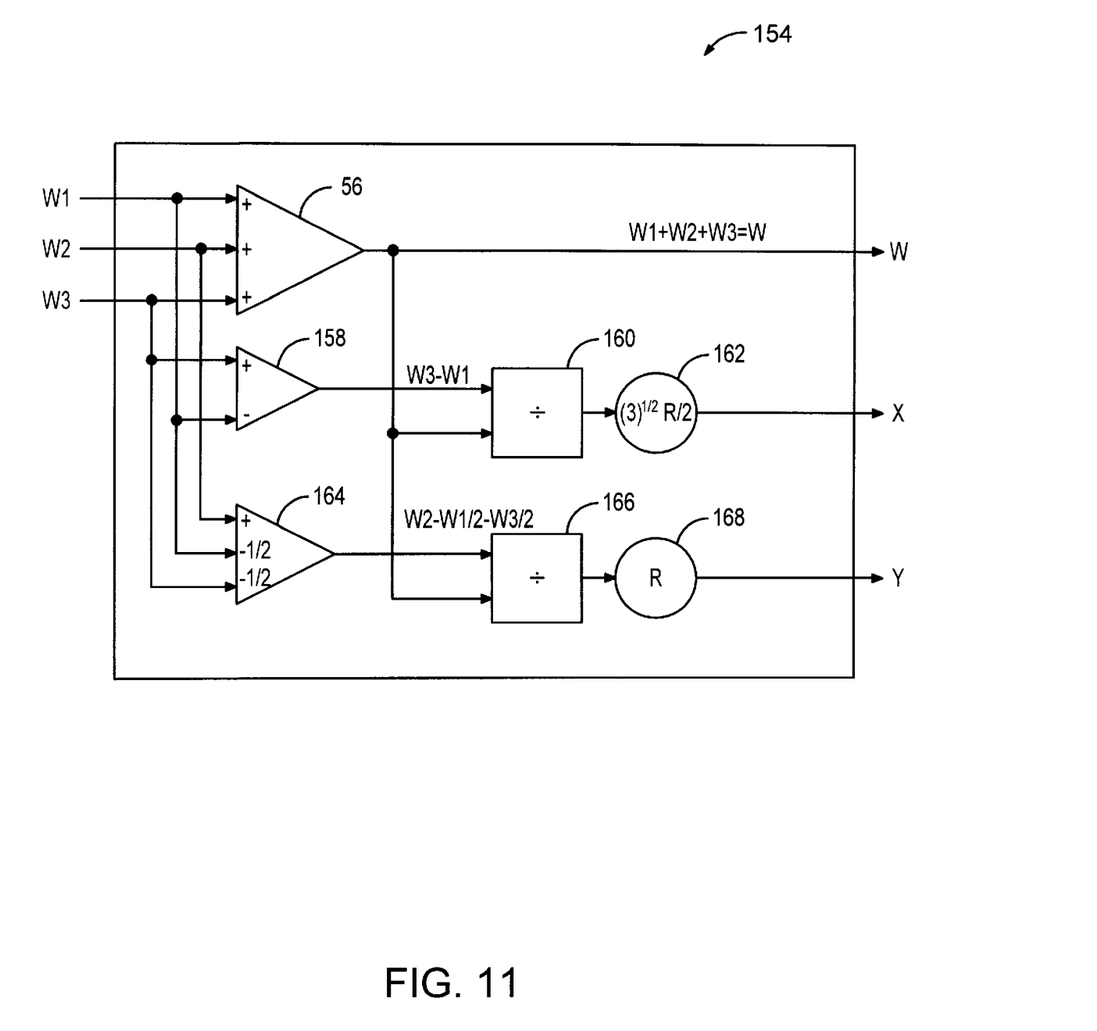
FIG. 11 is a block diagram of the components of a C.O.W. computer included in the functional status scale of FIG. 10.

The C.O.W. computer 154 is configured to use the equations (8) and (9) to derive x and y coordinates. In FIG. 11, the components of the C.O.W. computer are shown in a block diagram form. The C.O.W. computer includes a summing unit 156 that computes the W by summing the weight signals W1, W2 and W3 from the weight sensors 148, 150 and 152. The C.O.W. computer also includes a subtraction unit 158, a divider 160 and a multiplier 162 that compute the x coordinate of the C.O.W., using the weight signals W1 and W3 and the computed W. The C.O.W. computer further includes a subtraction unit 164, a divider 166 and a multiplier 168 that compute the y coordinate of the C.O.W., using the weight signals W1, W2 and W3 and the computed W. These computed values, W, x coordinate and y coordinate, are transmitted to the processor 44 of the functional status scale 146 for signal processing.

Figure 12:
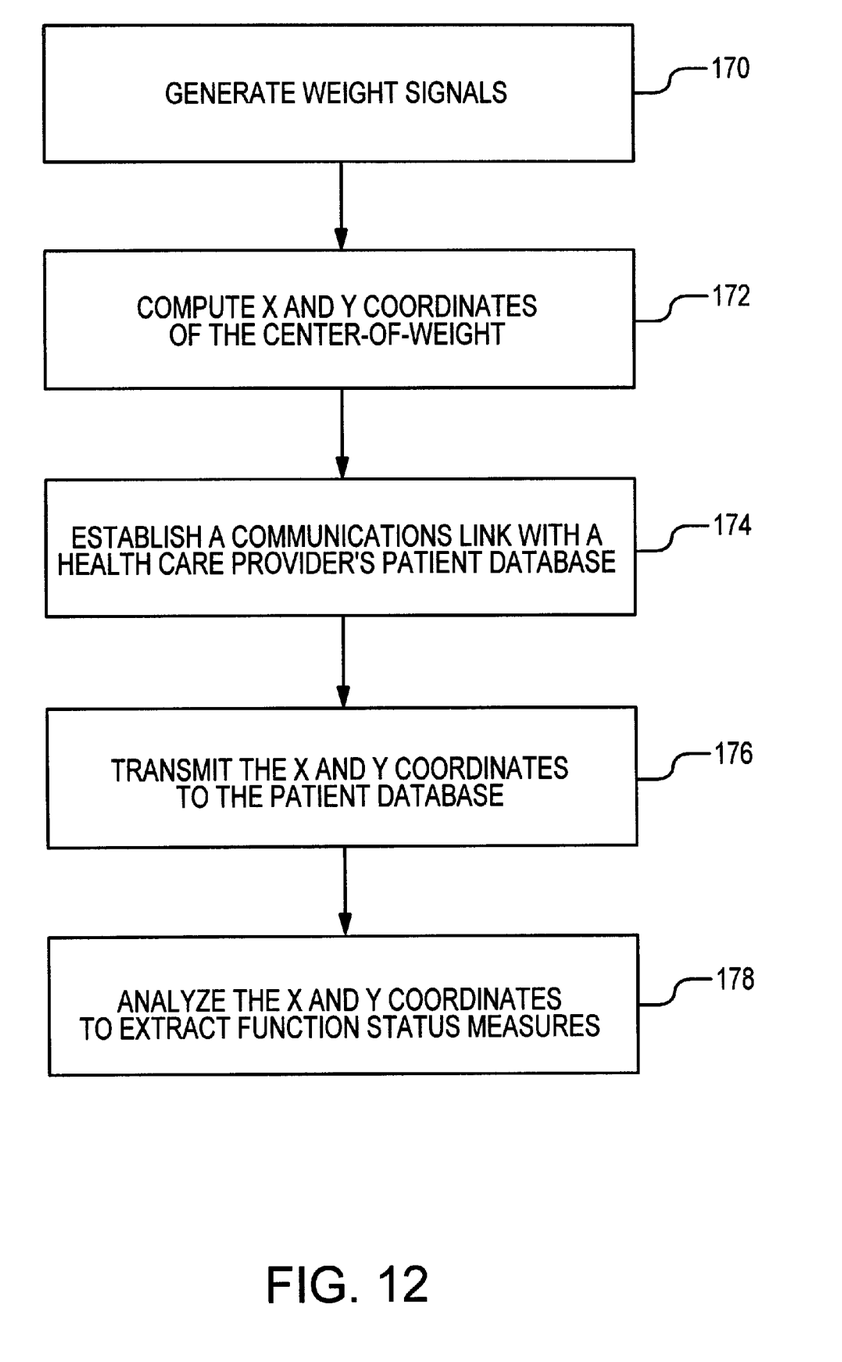
FIG. 12 is a flow diagram of a method of objectively assessing the functional status of a subject in accordance with the invention.

A method of objectively assessing the functional status of a subject in accordance with the invention will be described with reference to FIG. 12. During step 170, weight signals are generated by weight sensors of a functional status scale in response to the subject's weight when the subject is standing on the scale. Using the weight signals, x and y coordinates of the center-of-weight are then computed by a C.O.W. computer of the functional status scale, during step 172. Next, a communications link is established between the functional status scale and a health care provider's patient database, during step 174. The x and y coordinates are then transmitted to the health care provider's patient database during step 176. Next, during step 178, the x and y coordinates are analyzed by one or more analysis modules included in a remote computer that has communicated with the health care provider's patient database. During this step, functional status measures are extracted from the x and y coordinates by the analysis modules. The functional status measures may be derived by statistical analysis, frequency domain analysis or other analytical approaches. These functional status measures provide objective criteria in the assessment of the current functional status of the subject.

What is claimed is:

1. A system for assessing a physical status of a subject comprising:
    a platform having a surface;
    a plurality of pressure-sensitive sensors operatively coupled to said platform, said pressure-sensitive sensors being configured to generate signals in response to a force exerted on said surface by said subject situated on said platform;
    circuitry operatively coupled to said pressure-sensitive sensors to receive said signals, said circuitry being configured to derive center-of-weight data using said signals from said pressure-sensitive sensors;
    a remote device operatively coupled to said circuitry to provide information derived from said center-of-weight data, said information being indicative of said physical status of said subject;
    telecommunications devices connected to said circuitry and to said remote device to selectively link said circuitry and said remote device via a telecommunications network, thereby enabling exchanges of data therebetween; and
    an analysis module operatively coupled to said circuitry, said analysis module being configured to statistically extract said information from said center-of-weight data to yield at least two of (1) maximum x and y coordinate values as applied to said platform, (2) autocovariances of said x and y coordinate values, (3) autocovariances of response times, (4) standard deviations of said x and y coordinate values, (5) mean magnitude excursions of said x and y coordinates values, (6) maximum rates of change of said x and y coordinate values, (7) cross correlation coefficients between said x and y coordinate values, (8) cross covariances between said x and y coordinates values and (9) cross covariance lengths of said x and y coordinate values.

2. The system of claim 1 wherein said analysis module is configured to perform operations to extract said information from said center-of-weight data when said center-of-weight data is in the time domain and is configured to yield said extracted information in the frequency domain.

3. The system of claim 1 further comprising computer memory for storing said information for subsequent analysis by said analysis module and wherein said analysis module is a component of said remote device.

4. The system of claim 1 wherein said plurality of pressure-sensitive sensors includes four pressure-sensitive sensors that are positioned in a rectangular configuration, and wherein said circuitry is electrically configured to compute first and second coordinates of center-of-weight using signals from said four pressure-sensitive sensors.

5. The system of claim 1 wherein said plurality of pressure-sensitive sensors includes four pressure-sensitive sensors that are positioned in a diamond configuration, and wherein said circuitry is electrically configured to compute first and second coordinates of center-of-weight using signals from said four pressure-sensitive sensors.

6. The system of claim 1 wherein said plurality of pressure-sensitive sensors includes three pressure-sensitive sensors that are positioned in a triangular configuration, and wherein said circuitry is electrically configured to compute first and second coordinates of center-of-weight using signals from said three pressure-sensitive sensors.

7. The system of claim 1 wherein said remote device is operatively coupled to a network of computers.

8. A method of assessing a physical status of a subject comprising steps of:
    generating signals that correspond to forces being exerted on a platform by said subject;
    computing center-of-weight data by processing said signals, said center-of-weight data being in the time domain;
    establishing a communications link between said platform and a remote device; and
    analyzing said center-of-weight data to extract measures that are indicative of said physical status of said subject, including determining frequency domain measures from said center-of-weight data, and including performing operations at said remote device to extract statistical measures that are indicative of said physical status of said subject, said statistical measures including at least two of (1) maximum x and y coordinate values as applied to said platform, (2) autocovariances of said x and y coordinate values, (3) autocovariances of response times, (4) standard deviations of said x and y coordinate values, (5) mean magnitude excursions of said x and y coordinates values, (6) maximum rates of change of said x and y coordinate values, (7) cross correlation coefficients between said x and y coordinate values, (8) cross covariances between said x and y coordinates values and (9) cross covariance lengths of said x and y coordinate values.

9. The method of claim 8 wherein said signals are generated by four weight sensors that are operatively coupled to said platform, said four weight sensors being positioned in a rectangular configuration.

10. The method of claim 8 wherein said signals are generated by four weight sensors that are operatively coupled to said platform, said four weight sensors being positioned in a diamond configuration.

11. The method of claim 8 wherein said signals are generated by three weight sensors that are operatively coupled to said platform, said three weight sensors being positioned in a triangular configuration.

12. A method of assessing a physical status of a subject comprising steps of:
    generating signals that correspond to forces being exerted on a platform by said subject;
    computing center-of-weight data by processing said signals, said center-of-weight data being in the time domain;
    establishing a communications link between said platform and a remote device; and analyzing said center-of-weight data to extract measures that are indicative of said physical status of said subject, including determining frequency domain measures from said center-of-weight data, and including performing operations at said remote device to extract said frequency domain measures as measures of dominant frequency to one of the x and y coordinates related to said platform and a phase of said dominant frequency.

13. The method of claim 12 wherein said signals are generated by four weight sensors that are operatively coupled to said platform, said four weight sensors being positioned in a rectangular configuration.

14. The method of claim 12 wherein said signals are generated by four weight sensors that are operatively coupled to said platform, said four weight sensors being positioned in a diamond configuration.

15. The method of claim 12 wherein said signals are generated by three weight sensors that are operatively coupled to said platform, said three weight sensors being positioned in a triangular configuration.

* * * * *